United States Patent [19]

Neidig et al.

[11] 4,232,326
[45] Nov. 4, 1980

[54] CHEMICALLY SENSITIVE FIELD EFFECT TRANSISTOR HAVING ELECTRODE CONNECTIONS

[75] Inventors: Arno Neidig, Plankstadt; Gerhard Popp; Gabriele Gilbers, both of Lampertheim, all of Fed. Rep. of Germany

[73] Assignee: BBC Brown, Boveri & Company, Limited, Baden, Switzerland

[21] Appl. No.: 928,309

[22] Filed: Jul. 26, 1978

[30] Foreign Application Priority Data

Aug. 11, 1977 [DE] Fed. Rep. of Germany ....... 2736200

[51] Int. Cl.² .................. H01L 29/78; H01L 29/34; H01L 23/48
[52] U.S. Cl. ...................... 357/23; 357/52; 357/55; 357/65; 357/68; 357/73
[58] Field of Search ............. 357/23, 42, 54, 52, 357/55, 68, 65, 73

[56] References Cited

U.S. PATENT DOCUMENTS

| | | | |
|---|---|---|---|
| 4,097,314 | 6/1978 | Schlesier | 357/42 |
| 4,148,046 | 4/1979 | Hendrickson | 357/42 |
| 4,158,807 | 6/1979 | Senturia | 357/23 |

OTHER PUBLICATIONS

Potassium Ion-Sensitive Field Effect Transistor by Moss et al., Analytical Chemistry, vol. 47, No. 13, Nov. 1975, pp. 2238-2243.

*Primary Examiner*—Andrew J. James
*Attorney, Agent, or Firm*—Oblon, Fisher, Spivak, McClelland & Maier

[57] ABSTRACT

A chemically sensitive field effect transistor (FET), particularly an ion-sensitive FET (ISFET), and a method of making the same, wherein a semi-conductor body of a first conductivity type is provided with source and drain diffusion zones spaced apart and extending a predetermined distance into the semiconductor body from the front face thereof. Also formed in the semiconductor body is a pair of connection zones extending from the front face to the rear face of the semiconductor body, and connected to the diffusion zones on the front face by means of conductor paths, the diffusion zones, the conduction paths, and the connection zones formed of a material having a second conductivity and which are of a second conduction type with opposite polarity to the conduction type of the semiconductor body. External connections are made to the diffusion zones through the conductor paths and the connection zones by means of connection lines contacting the connection zones at the rear face of the semiconductor body.

5 Claims, 2 Drawing Figures

CHEMICALLY SENSITIVE FIELD EFFECT TRANSISTOR HAVING ELECTRODE CONNECTIONS

BACKGROUND OF THE INVENTION

1. Field of the Invention

This invention relates to a chemically sensitive field effect transistor, particularly an ion-sensitive field-effect transistor.

2. Description of the Prior Art

A known chemically sensitive "field-effect transducer", (for terminology see: ETZ-A, Vol. 16 (1964), No. 23, P. 682), of this kind (German Offenlegungsschrift No. 26 10 530, and also Biomedical Engineering, July 1976, pages 241 to 245) does not have a metal gate electrode integrated in the semiconductor body, unlike a likewise known device specially intended for detecting hydrogen (German Offenlegungsschrift No. 25 40 161). On the contrary, its chemically sensitive and selective layer is brought into contact with the material being examined by means of a preferably aqueous solution in which a reference electrode is immersed. The sensitive layer interacts with determined substances in the aqueous solution, so that in this way an electric field produced between source and drain in the semiconductor material is modulated in accordance with the chemical properties of the substance. These variations can be detected by an amplifier such as is known for example from IEEE Transactions on Biomedical Engineering, Vol. BME-19, No. 5, Sept. 1972, pages 342 to 351.

The industrial application of the field-effect transducer known from German Offenlegungsschrift No. 26 10 530 entails various problems. Apart from the fundamental problem of transferring the technique of chemically sensitive electrodes to semiconductor components, there is an additional technological problem. The chemically sensitive layer of the chemically sensitive transducer must be in direct contact with the conductive solution, which as previously mentioned is usually an aqueous solution, for example in the form of a pH-sensitive element, without any conductive connection being made between the transducer and the solution. In the planar technology customary at the present time, however, all electrical supply leads are disposed on a single surface of a semiconductor component of this kind, and in the known case the chemically sensitive layer is also situated on that surface. This gives rise to difficult insulation problems.

SUMMARY OF THE INVENTION

Accordingly, one object of this invention is to provide a novel field effect transistor of the kind first described above, wherein adequate insulation of the connections to the source and to the drain and of the transducer in general, particularly of its edge, is achieved while maintaining the previously described sensitivity for the substances which are to be examined.

This object is achieved in that according to the invention the aforesaid conductor paths are highly doped regions of the second conduction type which lead to zones which are of the same conduction type and same conductivity and are laterally offset in relation to the source and the drain, and that the last-mentioned zones extend to the rear face of the semiconductor body and are contacted there.

In a field-effect transducer of this kind the electrical supply leads for the source and drain can advantageously be taken to the rear side of the semiconductor body, so that when the front side of the sensitive layer on the semiconductor body comes into contact with the material to be examined there will be no faulty connections.

A conductive zone leading through the semiconductor body cannot be made by normal diffusion processes. In addition, the provision of zones of this kind solves only the insulation problems relating to the source and the drain. When the field-effect transducer is used in direct contact with aqueous solutions, the edge of the semiconductor body must also be adequately insulated, for which purpose the usual stabilization layers on the edges are not always adequate.

A further object therefore underlies the invention of providing a method of producing the chemically sensitive field-effect transducer by which the previously mentioned zones serving to insulate the source and the drain can be produced. In addition, insulation on the edges should be improved.

This object is achieved in that according to the invention the zones penetrating through the semiconductor body are produced by thermomigration, preferably by the thermomigration of aluminum into silicon of n-type conductivity.

The thermomigration for semiconductor components is known as such from IEEE Transactions on Electron Devices, Aug. 1976, pages 818 to 823. With regard to the method and mode of operation, reference is made to this publication. In the known case, however, only the production of pn-junctions is mentioned. According to the invention the known method is applied to the extension of the conductor paths to the rear face of the semiconductor body.

It is expedient for the method to be applied in the manner usual in semiconductor technology, starting from a large undivided slice of silicon, the front faces of the semiconductor bodies being at the same time stabilized by a thermal oxide, preferably silicon dioxide, and a diffusion barrier against undesired ions, preferably silicon nitride, while a layer of glass, preferably an alkali metal silicate glass, serves as the subsequently applied chemically sensitive layer. The combination of a film of silicon dioxide with a film of silicon nitride is known per se in another connection (German Offenlegungsschrift No. 24 31 917). In connection with ion-sensitive field-effect transistors (ISFET) a silicon dioxide layer is also already known as insulation (IEEE Transactions on Biomedical Engineering, Vol. BME-19, No. 5, Sept. 1972, pages 342–351). As in the first-mentioned known case, the silicon dioxide film stabilizes the electrical properties, while the silicon nitride film protects the semiconductor body against moisture and foreign substances.

For the insulation of the edges after the slice of silicon has been divided into the individual semiconductor bodies, each of the latter is advantageously cemented into an electrically insulating frame whose inner edge is covered by a glass serving as an edge stabilization layer and having a lower melting point than the glass of the sensitive layer.

These measures are particularly advantageous if the frame is at the same time a part of the casing of the finished semiconductor component.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
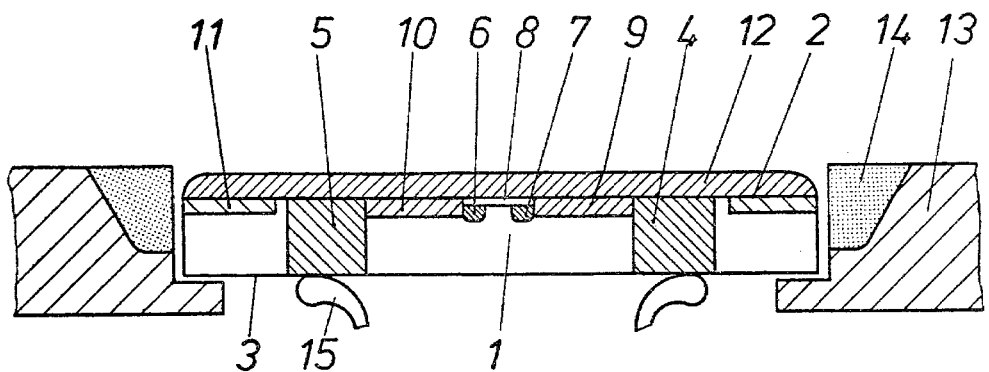
FIG. 1 is a diagrammatical section through the field-effect transistor transversely to the plane of the slice along the line 1—1 of FIG. 2.
Figure 2:
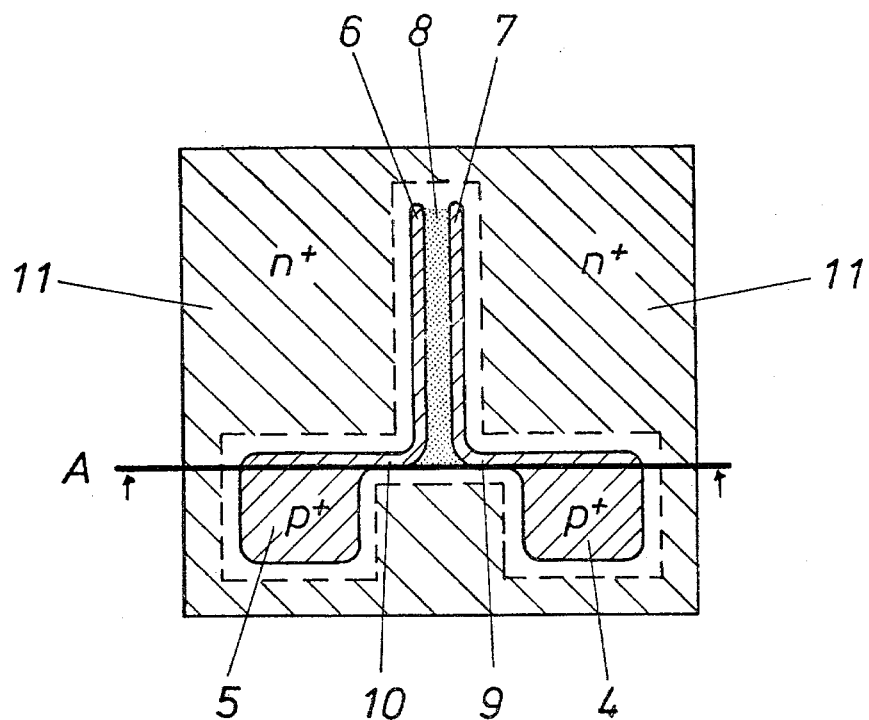
FIG. 2 is a plan view of the front face of the field-effect transistor without the stabilizing layer and without the sensitive layer.

Referring now to the drawings, wherein like reference numerals designate identical or corresponding parts throughout the several views, and more particularly to FIG. 1 thereof, there is seen a preferably rectangular semiconductor wafer 1 which consists of n-Si and has typical dimensions of about $1 \times 1$ mm$^2$ and a thickness of several 100 $\mu$m. This semiconductor wafer 1 is preferably a part of a larger Si slice of a diameter of from 50 to 100 mm which comprises several hundred similar components.

In each wafer 1 of the entire slice heavily p-doped zones 4 and 5 are produced simultaneously, extending from the front face 2 right through to the rear face 3, through the thermomigration of aluminum. Suitable structures for the field-effect transistor, source 6, and drain 7, and also optionally a flat channel 8 between source 6 and drain 7 are then produced by the usual methods of semiconductor technology. In addition, electrical connections are made between the source 6 and zone 5 and also between drain 7 and zone 4 by indiffusing heavily p-doped paths 9 and 10. For the electrical stabilization of the semiconductor structure a so-called channel limiter 11 may also be indiffused. The zones 4 and 5 have an adequately large cross-sectional area, which may selectively be rectangular or circular, so that these zones 4 and 5 can easily be electrically connected to external connections on the lower face 3 by the known thermocompression or ultrasonic methods.

Additional electronic components (amplifiers and the like), which can form a functional unit with the FET situated on the upper face 2, may also be integrated on the lower face 3 of the semiconductor wafer by known methods of semiconductor technology.

The application of a chemically sensitive layer 12 on the front face 2 and the fluid-tight encapsulation of the semiconductor wafer 1 are effected at suitable times during the production of the component. For example, a pH-sensitive glass layer 12 may be produced in the manner described below.

The chemically sensitive glass layer 12 is applied to the upper face 2 before the semiconductor slice is divided into individual wafers 1, and preferably after the stabilization of the FET on the upper face 2 by a thermal oxide, for example $SiO_2$, and a suitable diffusion barrier against undesired ions, for example $Si_3N_4$ (not shown). The following are possible methods of applying the pH-sensitive glass, for example alkali metal silicate glass:

(a) HF cathode atomization.
(b) Applying a glass powder suspension by fusion.
(c) Electron beam vaporization.
(d) Immersion in the molten glass. In this case the rear face 3 of the slice must be completely or partly etched free of the glass layer.
(e) Chemical deposition from the gas phase.

After the silicon slice has been divided into individual semiconductor wafers 1 (by laser or diamond scoring) the wafers 1 are firmly cemented in an electrically insulating frame 13. This is effected for example by securing them by fusion in a frame 13 covered by a thick low-melting glass 14 ($\sim 100$ $\mu$m layer thickness). The melting point of this insulating glass 14 should be lower than that of the pH-sensitive glass. The insulating glass 14 flows into the gaps between the semiconductor wafer 1 and the frame 13 and insulates the edge of the semiconductor wafer 1. The frame 13 may even be part of a casing or be installed in a casing. If possible it should partly engage under the rear face of the wafer 1. The electric connections 15 (Al or Au wires) which are to be attached to the lower face 3 of the wafer 1 by thermocompression or ultrasound may be connected to corresponding lead-ins in the casing.

Another possible method of fastening the semiconductor wafer 1 in a frame or casing involves placing the wafer with its front face 2 downwards into an opening of suitable size in the casing 1, this opening being covered by a low-melting insulating glass. When the casing is heated to the melting point of the insulating glass the wafer 1 is sealingly connected to the casing. The contacts 15 can then be applied. The casing 13 can thereupon easily be sealed (by sealing rings or the like) against the solution which is to be examined.

The utilization and mode of operation of the completed semiconductor component compares favorably with known ion-sensitive field-effect transistors, while however substantially better long-term stability is achieved through the insulations provided by the present invention.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. In a chemically sensitive field effect transistor (FET), particularly an ion-sensitive FET (ISFET), wherein a semiconductor body of a first conduction type, and having a front face and a rear face on opposite sides thereof, is provided with two diffusion zones, a source diffusion zone and a drain diffusion zone, which are spaced apart on and extend to a determined depth from said front face and which are formed of a second conduction type with opposite polarity to the first conduction type, and wherein said diffusion zones bound a channel and are connected to conductor paths which contact connection lines, said transistor having a stabilization layer on said front face, a chemically sensitive layer on said front face, and additional stabilization layers, particularly on the edges thereof, the improvement comprising:

said conductor paths connected to said diffusion zones formed of highly doped regions of the second conduction type; and a pair of connection zones respectively connected to said diffusion zones through said conductor paths, said connection zones laterally offset relative to said diffusion zones and extending through said semiconductor body from the front face to the rear face thereof, said connection lines contacting said connection zones at said rear face;

whereby said connection lines are connected to said diffusion zones through said connection zones and said conduction paths.

2. A chemically sensitive field effect transistor (FET), according to claim 1, further comprising:

said connection zones formed of the same conduction type and the same conductivity as said diffusion zones.

3. A chemically sensitive field effect transistor (FET), according to claim 1, further comprising:

a thermal oxide coating applied to the front face of said semiconductor body; and a chemically sensitive glass coating formed on the entire front face of the semiconductor body above said thermal oxide coating.

4. A chemically sensitive field effect transistor (FET), according to claim 1, further comprising:

an electrically insulating frame in which said semiconductor body is embedded, said frame having an inner edge coated with glass which has a lower melting point than the chemically sensitive layer and which serves as an edge-sided stabilization coating.

5. A chemically sensitive field effect transistor (FET), according to claim 3, further comprising:

an electrically insulating frame in which said semiconductor body is embedded, said frame having an inner edge coated with glass which has a lower melting point than the chemically sensitive glass coating and which serves as an edge-sided stabilization coating.

* * * * *